United States Patent
Koest et al.

(10) Patent No.: US 8,551,014 B2
(45) Date of Patent: Oct. 8, 2013

(54) OPHTHALMOLOGICAL ANALYSIS METHOD AND ANALYSIS SYSTEM

(75) Inventors: Gert Koest, Hannover (DE); Andreas Steinmueller, Wettenberg (DE)

(73) Assignee: Oculus Optikgeraete GmbH, Wetzlar-Dutenhofen (DE)

( * ) Notice: Subject to any disclaimer, the term of this patent is extended or adjusted under 35 U.S.C. 154(b) by 97 days.

(21) Appl. No.: 13/165,496

(22) Filed: Jun. 21, 2011

(65) Prior Publication Data

US 2011/0313273 A1 Dec. 22, 2011

(30) Foreign Application Priority Data

Jun. 21, 2010 (EP) .................... 10166681
Oct. 28, 2010 (DE) ............... 10 2010 049 633
Oct. 28, 2010 (DE) ............... 10 2010 049 634
May 31, 2011 (EP) .................... 11168232
May 31, 2011 (EP) .................... 11168234
May 31, 2011 (EP) .................... 11168235

(51) Int. Cl.
| | |
|---|---|
| *A61B 3/00* | (2006.01) |
| *A61B 3/10* | (2006.01) |
| *A61B 3/107* | (2006.01) |
| *A61B 3/113* | (2006.01) |
| *A61B 3/14* | (2006.01) |
| *A61B 3/16* | (2006.01) |

(52) U.S. Cl.
USPC ........... 600/558; 351/200; 351/212; 351/246; 600/398; 600/401; 600/405; 600/587

(58) Field of Classification Search
USPC .......... 351/200, 246, 212; 600/398, 401, 405, 600/558, 587
See application file for complete search history.

(56) References Cited

U.S. PATENT DOCUMENTS 3,406,681 A 10/1968 Zandman
5,614,966 A * 3/1997 Iijima et al. ............. 351/208

(Continued)

FOREIGN PATENT DOCUMENTS

CN 101653354 A 2/2010
DE 10 2006 039 893 A1 3/2007

(Continued)

OTHER PUBLICATIONS

European Search Report issued in corresponding application No. EP 11168232A, completed on Oct. 10, 2011 and mailed Oct. 19, 2011.

(Continued)

*Primary Examiner* — Sean Dougherty
(74) *Attorney, Agent, or Firm* — Griffin & Szipl, P.C.

(57) ABSTRACT

The invention relates to an opthalmological analysis method for measuring an intraocular pressure in an eye with an analysis system consisting of an actuating device, wherein the actuating device causes a puff of air to be applied to the eye in such manner that the cornea is deformed, an observation system with which the deformation of the cornea is observed and recorded, wherein sectional images of the cornea when it is deformed and not deformed are created with the observation device, and an analysis device with which the intraocular pressure is derived from the sectional images of the cornea, wherein a material characteristic of the cornea is derived from the sectional images of the cornea in the analysis device, wherein a diameter $d_1$ of a first applanation area of the cornea and a diameter $d_n$ of a deformation area of the cornea is derived as a material characteristic.

20 Claims, 4 Drawing Sheets

(56) References Cited

U.S. PATENT DOCUMENTS

Figures 1A, 1B, 1C, 1D, 1E:
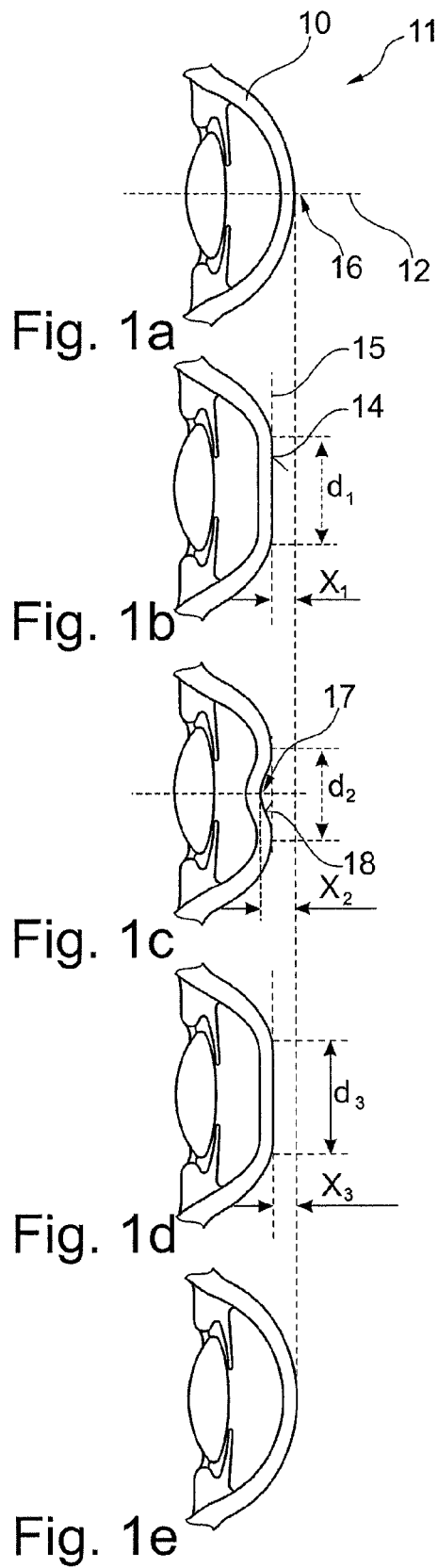

| | | | |
|---|---|---|---|
| 5,822,035 A | 10/1998 | Bille | |
| 6,120,444 A | 9/2000 | Miyakawa et al. | |
| 7,153,266 B2* | 12/2006 | Uchida | 600/399 |
| 7,235,051 B2* | 6/2007 | Iwanaga | 600/401 |
| 7,364,298 B2* | 4/2008 | Hayashi et al. | 351/212 |
| 7,481,767 B2 | 1/2009 | Luce | |
| 7,909,765 B2 | 3/2011 | Luce | |
| 8,152,302 B2 | 4/2012 | Bille | |
| 2004/0046936 A1* | 3/2004 | Iwanaga | 351/212 |
| 2005/0030473 A1 | 2/2005 | Fahrenkrug et al. | |
| 2006/0241367 A1 | 10/2006 | Koest | |
| 2007/0055122 A1 | 3/2007 | Luce | |
| 2007/0097317 A1* | 5/2007 | Hayashi et al. | 351/200 |
| 2007/0121120 A1 | 5/2007 | Schachar | |
| 2007/0146636 A1* | 6/2007 | Ishikura | 351/221 |
| 2009/0036761 A1* | 2/2009 | Abreu | 600/318 |
| 2009/0093698 A1 | 4/2009 | Luce | |
| 2009/0216106 A1* | 8/2009 | Takii | 600/401 |
| 2011/0032480 A1* | 2/2011 | Rathjen | 351/206 |
| 2011/0222021 A1* | 9/2011 | Rathjen | 351/214 |
| 2012/0162605 A1* | 6/2012 | Koest | 351/221 |
| 2012/0218518 A1* | 8/2012 | Wada | 351/208 |
| 2012/0310073 A1* | 12/2012 | Koest et al. | 600/401 |

FOREIGN PATENT DOCUMENTS

| | | |
|---|---|---|
| EP | 1 692 998 A1 | 8/2006 |
| JP | H10 213483 A | 8/1998 |
| JP | H10 309265 A | 11/1998 |
| JP | 2000254101 A | 9/2000 |
| JP | 2002-263069 A | 9/2002 |
| JP | 2006231052 A | 9/2006 |
| JP | 2007121174 A | 5/2007 |
| JP | 2008011878 A | 1/2008 |
| JP | 2009273715 A | 11/2009 |
| JP | 2012519553 A | 8/2012 |
| WO | 2007 056292 A3 | 5/2007 |

OTHER PUBLICATIONS

Kaneko, Makoto et al., "Dynamic Sensing of Human Eye," Proceedings of the 2005 IEEE, International Conference on Robotics and Automation, Apr. 2005, pp. 2871-2876.

Kempf, Roland et al., "Understanding eye deformation in non-contact tonometry," Proceedings of the 28th IEEE, EMBS Annual International Conference, Aug. 2006, pp. 5428-5431.

English Translation of Korean Intellectual Property Office Notice of Rejection issued in parallel application No. 10-2011-0060129, mailed on Dec. 7, 2012.

Actuator, McGraw-Hill Dictionary of Scientific and Technical Terms, (6th ed.) 2003, p. 32.

Office Action in parallel Australian application. Application No. 2011202972, issued Jan. 21, 2013.

English Translation of a Japanese Office Action in a parallel application. Application No. 2011-136552, issued Feb. 1, 2013.

Chinese Office Action in Chinese parallel case No. 2011/10169734.9 dated May 6, 2013 and received Jun. 14, 2013 w/English Translation.

English Translation of a Japanese Office Action relating to a parallel Japanese action (2011 136548), drafted Jun. 5, 2013 and received Jun. 10, 2013.

English Translation of a Chinese Office Action with search report relating to a parallel Chinese action (2011 10169822.9) issued May 30, 2013.

"An Experimental Observation of Photoelastic Stress of Human Joint at Different Flex Angle," Journal of Applied Biomechanics, vol. 13, No. 4, Dec. 1998, with English Abstract.

"Photoelastic technology is used to measure stress," Electronic Test, Jan. 2009, No. 2; Feng Xiaoqin, Song Wen'ai, Ma Jinhong, (North University of China, Key laboratory of instrumentation science and dynamic measurement, Taiyuan 030051 China), with English Abstract.

* cited by examiner

OPHTHALMOLOGICAL ANALYSIS
METHOD AND ANALYSIS SYSTEM

This is a U.S. Patent Application which claims priority from European Patent Application No. 10166681.6, filed Jun. 21, 2010, German patent Application No. 10 2010 049 634.0, filed Oct. 28, 2010, German patent Application No. 10 2010 049 633.2, filed Oct. 28, 2010, European Patent Application No. 11168235.7, filed May 31, 2011, European Patent Application No. 11168232.4, filed May 31, 2011, and European Patent Application No. 11168234.0, filed May 31, 2011. The entire disclosures of the above patent applications are hereby incorporated by references.

FILED OF THE INVENTION

The invention relates to an opthalmological analysis method for measuring an intraocular pressure in an eye with an analysis system, including an analysis system of such kind consisting of an actuating device, with which an eye cornea is deformed in contactless manner, wherein a puff of air is applied to the eye via the actuating device to deform the cornea, an observation system that is used to observe and record the corneal deformation, wherein sectional images of the cornea with and without deformation are recorded with the observation system, and an analysis device that is used to derive the intraocular pressure from the sectional images of the cornea.

BACKGROUND OF THE INVENTION

Analysis methods and systems of such kind are sufficiently known and are used primarily to obtain the most accurate contactless measurement possible of intraocular pressure in an eye. For example, a non-contact tonometer is used for this purpose, with the aid of which a puff of air is applied to the eye being examined, wherein an intensity of the air puff is selected such that the cornea of an eye is pressed inwards, creating a concave surface shape. The cornea briefly forms a flat surface before maximum deformation of the cornea is reached and before the cornea is indented towards the lens of the eye, this surface being called the first applanation point. After maximum deformation of the cornea has been reached and the cornea has returned to its original shape, the cornea passes through a second applanation point of the same kind. Now the intraocular pressure may be calculated by plotting a pressure of the air puff against the development of the corneal applanation over time. The measured values obtained with the non-contact tonometer are set in relation to comparison measured values that have been determined using an applanation tonometer or contact tonometer that produces relatively more accurate measurements, thus enabling a an internal eye pressure to be derived that approximates the actual intraocular pressure more closely as the result.

However, an intraocular pressure that is measured with a non-contact tonometer is not sufficiently accurate compared with a pressure measurement made with an applanation tonometer, because the measurement is distorted by the cornea, among other reasons. In order to improve the measurement accuracy, it was therefore attempted to take the influence of the cornea on the measurement into account, for example with a thickness measurement or measurement of corneal radii before conducting the measurement with a non-contact tonometer. It is also known to consider a modulus of elasticity or Young's modulus as a biomechanical property of the cornea, and to adjust the measurement in question with a corresponding calculation factor. In this context, it is assumed that the modulus of elasticity is always of the same magnitude and is thus constant for all measurements, even for different eyes. It is further assumed that the modulus of elasticity is the same for all areas of a given cornea. Consideration of a modulus of elasticity in a non-contact tonometer measurement has the disadvantage that this material characteristic or material parameter is used to characterise a tensile load, which does not occur with non-contact tonometer measurements. Moreover, a modulus of elasticity varies individually from one eye to the next and also as a function of the respective areas of the cornea within the cornea itself. Therefore, consideration of material parameters of such kind and calculation of a measurement result may still not lead to measurement results of satisfactory accuracy.

It is further known to incorporate the biomechanical properties of a cornea in a non-contact tonometer measurement during the measurement or to calculate these properties as the measurement is being conducted. For this, a puff of air is applied to the cornea, and a pump pressure is recorded continuously during the course of the measurement by a pressure sensor. A timeline of the measurement is also recorded, and first and second corneal applanation points are detected optically. An intraocular pressure may now be derived for example by determining the pressures prevailing respectively at the times of the first and second applanations, particularly since the forces necessary to deflect the cornea both inwardly and outwardly are assumed to be of the same magnitude, and thus cancel one another out. Consequently an intraocular pressure is derived from an average of the force applied for pressing the cornea inwards and outwards, in the form of the air puff.

Alternatively, it is known to determine a hysteresis point between the first and second applanation points and to derive and correct the intraocular pressure on the basis of the hysteresis measurement. In the hysteresis measurement, the first and second applanation points are detected optically and correlated with a timeline of a pressure curve of a pump, that is to say an associated time value and a pressure value is determined for each applanation point. Since the cornea is depressed inwards and the first applanation point is reached at a higher pressure than when cornea is deflected outwards again and the second applanation point is reached, this pressure difference may be used to determine the hysteresis as a material characteristic of the cornea.

The disadvantage of these measurement methods is that a movement of the cornea caused by a puff of air is subject to dynamic effects, which may distort such time/pressure measurements, particularly since the dynamic effects of the described non-contact tonometer measurements cannot be taken into account. In order to avoid such undesirable vibrations of the cornea, a speed of the air puff is minimised as far as possible to avoid distortion of the measurement result due to undesirable movement of the cornea. It is also necessary to synchronise the start of the air puff with the required time measurement. However, when a mechanical pump such as a piston pump is used to generate the air puff, it is not possible to synchronise the times with this degree of accuracy, because of the effects of inertia or friction for example, again leading to a distortion of the measurement result. Moreover, as was indicated earlier, the air puff is pressure-monitored, which means it is altered as required while the measurement is taking place. Thus the air puff is reduced or switched off after the first applanation point has been exceeded to prevent the cornea from being deflected inwards too far. However, this requires continuous monitoring of both the pump pressure and of the course thereof over time relative to the time points of the first and second applanation points, which in turn gives rise to a number of possible sources of error that might distort a measurement result. In summary, therefore, the analysis methods and systems known from the prior art, based on pressure and time measurement systems that operate independently of and parallel with one another with simultaneous detection of the applanation points, are still rather inaccurate compared with a measurement carried out using a contact tonometer.

SUMMARY OF THE INVENTION

The task underlying the present invention is therefore to suggest an opthalmological analysis method for measuring an intraocular pressure in an eye and a system for performing such analysis, with which comparatively improved measurement accuracy may be achieved.

This task is solved according to the invention with the characteristics of an opthalmological analysis method in that the opthalmological analysis method measures an intraocular pressure in an eye (11) with an analysis system consisting of an actuating device with which a cornea (10) of the eye is deformed in contactless manner, wherein the actuating device causes a puff of air to be applied to the eye in such manner that the cornea is deformed, an observation system with which the deformation of the cornea is observed and recorded, wherein sectional images are created of the cornea when it is deformed and not deformed, and an analysis device with which the intraocular pressure is derived from the sectional images of the cornea, characterized in that a material characteristic of the cornea is derived from the sectional images of the cornea in the analysis device, wherein a diameter $d_1$ of a first applanation area (14) of the cornea and a diameter $d_n$ of a deformation area of the cornea differing from the first applanation area is derived as a material characteristic, wherein the intraocular pressure is derived taking into account the material characteristics of the cornea. Additional, particularly beneficial embodiments of the invention are provided in accordance with the following subsidiary opthalmological analysis methods.

In accordance with a second opthalmological analysis method embodiment of the invention, the first embodiment is modified so that a material characteristic of the cornea (10) that is independent of the intraocular pressure is derived. In accordance with a third opthalmological analysis method embodiment of the invention, the first embodiment and the second embodiment are modified so that a pump pressure for producing an air puff progresses in the form of a bell curve (13) relative to a duration thereof. In accordance with a fourth opthalmological analysis method embodiment of the invention, the first embodiment, the second embodiment, and the third embodiment are modified so that a maximum pump pressure for creating the air puff is the same in preceding and following measurements. In accordance with a fifth opthalmological analysis method embodiment of the invention, the first embodiment, the second embodiment, the third embodiment, and the fourth embodiment are modified so that a pump pressure for creating the air puff is measured when an applanation point of the cornea (10) is reached. In accordance with a sixth opthalmological analysis method embodiment of the invention, the first embodiment, the second embodiment, the third embodiment, the fourth embodiment, and the fifth embodiment are modified so that a speed of movement of the cornea (10) is measured for the purpose of deriving the material characteristic. In accordance with a seventh opthalmological analysis method embodiment of the invention, the first embodiment, the second embodiment, the third embodiment, the fourth embodiment, the fifth embodiment, and the sixth embodiment are modified so that a maximum deformation of the cornea (10) is derived from the sectional images measured for the purpose of deriving the material characteristic. In accordance with an eighth opthalmological analysis method embodiment of the invention, the seventh embodiment is modified so that a diameter d2 of a deformation area (18) of the cornea (10) is determined for a maximum deformation of the cornea in the direction of an optical axis (12) for the purpose of deriving the material characteristic. In accordance with a ninth opthalmological analysis method embodiment of the invention, the first embodiment, the second embodiment, the third embodiment, the fourth embodiment, the fifth embodiment, the sixth embodiment, the seventh embodiment, and the eighth embodiment are modified so that a parameter of a flat applanation area (14, 18) is measured when an applanation point of the cornea (10) is reached for the purpose of deriving the material characteristic. In accordance with a tenth opthalmological analysis method embodiment of the invention, the first embodiment, the second embodiment, the third embodiment, the fourth embodiment, the fifth embodiment, the sixth embodiment, the seventh embodiment, the eighth embodiment, and the ninth embodiment are modified so that a ratio between the diameter $d_1$ of the first applanation area (14) of the cornea (10) and a diameter $d_3$ of a second applanation area of the cornea is determined for the purpose of deriving the material characteristic. In accordance with an eleventh opthalmological analysis method embodiment of the invention, the first embodiment, the second embodiment, the third embodiment, the fourth embodiment, the fifth embodiment, the sixth embodiment, the seventh embodiment, the eighth embodiment, the ninth embodiment, and the tenth embodiment are modified so that an amplitude of the deformation of the cornea (10) is derived from the sectional images of the cornea for the purpose of deriving the material characteristic. In accordance with a twelfth opthalmological analysis method embodiment of the invention, the first embodiment, the second embodiment, the third embodiment, the fourth embodiment, the fifth embodiment, the sixth embodiment, the seventh embodiment, the eighth embodiment, the ninth embodiment, the tenth embodiment, and the eleventh embodiment are modified so that a curvature of the cornea (10) with and/or without deformation is derived from the sectional images of the cornea for the purpose of deriving the material characteristic. In accordance with a thirteenth opthalmological analysis method embodiment of the invention, the first embodiment, the second embodiment, the third embodiment, the fourth embodiment, the fifth embodiment, the sixth embodiment, the seventh embodiment, the eighth embodiment, the ninth embodiment, the tenth embodiment, the eleventh embodiment, and the twelfth embodiment are modified so that the deformation of the cornea (10) is continued by a free oscillation of the cornea, and that the free oscillation of the cornea is determined as a further material characteristic. In accordance with a fourteenth opthalmological analysis method embodiment of the invention, the thirteenth embodiment is modified so that a frequency and/or amplitude of the free oscillation are measured. In accordance with a fifteenth opthalmological analysis method embodiment of the invention, the first embodiment, the second embodiment, the third embodiment, the fourth embodiment, the fifth embodiment, the sixth embodiment, the seventh embodiment, the eighth embodiment, the ninth embodiment, the tenth embodiment, the eleventh embodiment, the twelfth embodiment, the thirteenth embodiment, and the fourteenth embodiment are modified so that a stiffness of the cornea (10) is derived as a material characteristic. In accordance with a sixteenth opthalmological analysis method embodiment of the invention, the first embodiment, the second embodiment, the third embodiment, the fourth embodiment, the fifth embodiment, the sixth embodiment, the seventh embodiment, the eighth embodiment, the ninth embodiment, the tenth embodiment, the eleventh embodiment, the twelfth embodiment, the thirteenth embodiment, the fourteenth embodiment, and the fifteenth embodiment are modified so that a stress in the material of the cornea (10) is derived as a material characteristic. In accordance with a seventeenth opthalmological analysis method embodiment of the invention, the first embodiment, the second embodiment, the third embodiment, the fourth embodiment, the fifth embodiment, the sixth embodiment, the seventh embodiment, the eighth embodiment, the ninth embodiment, the tenth embodiment, the eleventh embodiment, the twelfth embodiment, the thirteenth embodiment, the fourteenth embodiment, the fifteenth embodiment, and the sixteenth embodiment are modified so that material characteristics that differ from each other are each assigned to different regions of the cornea (10). In accordance with an eighteenth opthalmological analysis method embodiment of the invention, the first embodiment, the second embodiment, the third embodiment, the fourth embodiment, the fifth embodiment, the sixth embodiment, the seventh embodiment, the eighth embodiment, the ninth embodiment, the tenth embodiment, the eleventh embodiment, the twelfth embodiment, the thirteenth embodiment, the fourteenth embodiment, the fifteenth embodiment, the sixteenth embodiment, and the seventeenth embodiment are modified so that the observation system comprises a camera and an illumination device in a Scheimpflug arrangement, wherein the sectional images are taken with the camera.

This task is also solved according to the invention with the characteristics of an opthalmological analysis system in that the opthalmological analysis system for measuring an intraocular pressure in an eye (11), comprises an actuating device with which a cornea (10) of the eye can be deformed in contactless manner, wherein the actuating device causes a puff of air to be applied to the eye in such manner that the cornea is deformed, an observation system with which the deformation of the cornea can be observed and recorded, wherein sectional images of the cornea when it is deformed and not deformed can be created with the observation system, and an analysis device with which the intraocular pressure can be derived from the sectional images of the cornea, characterized in that a material characteristic of the cornea is derived from the sectional images of the cornea in the analysis device, wherein a diameter $d_1$ of a first applanation area (14) of the cornea and a diameter $d_n$ of a deformation area of the cornea differing from the first applanation area is derived as a material characteristic, wherein the intraocular pressure is derived taking into account the material characteristics of the cornea.

In the opthalmological analysis method according to the invention for measuring an intraocular pressure in an eye with an analysis system, generally, the analysis system includes an actuating device with which the cornea of the eye is deformed in contactless manner, wherein the actuating device causes a puff of air to be applied to the eye in such manner that the cornea is deformed, an observation system with which the deformation of the cornea is observed and recorded, wherein sectional images of the cornea when it is deformed and not deformed are created with the observation system, and an analysis device with which the intraocular pressure is derived from the sectional images of the cornea, wherein a material characteristic of the cornea is derived from the sectional images of the cornea in the analysis device, wherein a diameter $d_1$ of a first applanation area of the cornea and a diameter $d_n$ of a deformation area of the cornea differing from the first applanation area a of the cornea is derived as a material characteristic, wherein the intraocular pressure is derived taking into account the material characteristics of the cornea.

When the cornea is deformed by the air puff, the cornea is completely flattened, in which case the first applanation area is formed having diameter $d_1$. The applanation area is then essentially flat and in the region of an applanation plane lies orthogonally to an optical axis of the eye or a device axis of an analysis system. While the cornea is deformed, a concave depression that differs significantly from the first applanation area is formed in the cornea. If the deformation area of the depression differing from the first applanation area is compared with the first applanation area, a material characteristic of the cornea may be defined, since the formation of the deformation area is dependent on the material characteristic. The material characteristic thus relates not to a generally known material characteristic but is based solely on a definition of two differing geometries of the deformed cornea. In this case, the first applanation area or diameter $d_1$ of the first applanation area is a reference scale for the deviation. If the comparison is made with diameter $d_n$ of the corneal deformation area, this comparison may be made particularly easily. Diameter $d_n$ may be determined very easily, particularly in the case of a deformation movement of the cornea after passing the first applanation area or a first applanation point, since the deformation area then assumes a concave shape. It is further provided that the deformation area or diameter $d_n$ in a specified time period of the deformation relative to the first applanation area, or even another measurable point or position of the cornea during the deformation is used to define the deviating deformation area of the cornea. The calculated deviation and the relative values of the pertinent diameters are also stored in a database and compared. Thus, an objective intraocular pressure or also a corresponding correction value is known for the values stored in the database, so that the objective intraocular pressure of the eye being measured is derived taking into account the geometrically defined material characteristic of the cornea.

It should also be noted that with the method it is not necessary to measure the pump pressure. Accordingly, any measurement of an intraocular pressure is always carried out with the same, constant pump pressure. Since there is no need to vary the level of the pump pressure or synchronise the time of the pump pressure, a number of possible sources of error may be eliminated and the measurement may be carried out with a particularly high degree of accuracy. The material characteristic of the cornea determined in this way may be used in other ways in the context of refractive eye surgery as well, for example to match the respective cornea properties in a LASIK procedure.

The material characteristic may also be derived as a material characteristic of the cornea independent of intraocular pressure. In this way, the intraocular pressure and the corneal material characteristic may then be determined particularly accurately separately from one another as independent material characteristics describing the cornea.

It is also advantageous if a pump pressure for generating the puff of air follows the course of a bell curve with regard to a temporal duration thereof. In this way, the pump pressure may affect the cornea in the form of the puff of air identically and entirely uninfluenced by other factors for each individual measurement. In this context, the bell curve may also have a symmetrical shape among other characteristics.

A maximum pump pressure for generating the puff of air may also be the same as for preceding and subsequent measurements. In this way, particularly good comparability between different measurements may be achieved. The maximum pump pressure may be 70 mm Hg, for example.

Even so, in order to be able to correct a pump pressure or check a desired pressure profile if necessary, a pump pressure for generating a puff of air may be measured when an applanation point of the cornea is reached. For example, a pump may be equipped with a pressure sensor that enables the pump pressure to be monitored throughout the duration of the entire measurement. This enables possible errors in terms of the pump pressure to be eliminated during measurement and the continuity of consecutive measurements to be assured.

A period of time between the start and end of the deformation of the cornea may also be measured to enable the material characteristic to be derived. In particular, it then becomes possible to assign all of the sectional images recorded to a given point of time in the measurement, so that the chronological sequence of the deformation may be tracked. In particular, a point in time of the first and second applanations of the cornea and therewith also a temporal offset between them may be determined precisely. Thus, the calculation of this time period may also be sufficient for determining the pertinent material characteristic. In addition, a time period of the entire deformation of the cornea may be used for deriving the material characteristic.

A speed of the movement of the cornea may be measured to derive the material characteristic. In particular, if the temporal progression of a deformation of the cornea is known, a dynamic of the deformation may also be examined, so that particular dynamic effects may be evaluated with respect to the respective material characteristic. For example, post-oscillation of the cornea after an air puff no longer has the effect of distorting the measurement result if the post-oscillation is taken into account during the measurement. Moreover, a speed of an air puff relative to otherwise undesirable dynamic effects is also freely selectable for a measurement. It is also possible to draw conclusions about an indentation depth or maximum amplitude on the basis of the measured speed, since a functional relationship exists between these parameters.

In order to determine the material characteristic yet more accurately, a maximum deformation of the cornea may be derived from the sectional images for deriving the material characteristic. Accordingly, a maximum indentation depth of the cornea may be determined from the sectional images, in which case a supplementary point in time of maximum corneal deformation may be established at least relative to one of the applanation points.

In order to derive the material characteristic, a diameter $d_2$ of a deformation area of the cornea may be determined for a maximum deformation of the cornea in the direction of a visual axis or a device axis. The maximum corneal deformation may be determined from a series of sectional images of the deformed cornea. In this way, it is possible to define a point in time of the definition or a geometry of the cornea for each measurement, which may be used as a reference for comparison with the first applanation area of the cornea. Diameter $d_2$ may then also be determined simply by defining it as an distance between two opposite points in a longitudinal sectional plane of the cornea when the cornea is in the state of maximum deformation, wherein each of the points represents the points closest to the analysis system. These points may be taken from a sectional image and accordingly represent diameter $d_2$ of the maximum corneal deformation.

Optionally, a parameter of a flat applanation area may also be measured in order to derive the material characteristic when a corneal applanation point is reached. For example, a parameter of the applanation area or the diameter thereof and/or its shape may be considered as an indicator of the stiffness of the cornea. The corneal radii adjacent to the respective applanation area may also be used as an additional indicator.

In order to derive the material characteristic, a ratio may be determined between diameter $d_1$ of the first applanation area of the cornea and a diameter $d_3$ of a second applanation area of the cornea. During deformation of the cornea by the air puff the cornea is depressed inwards, forming the first applanation area, until it reaches a maximum deformation of the cornea with a concave depression, and the cornea subsequently springs back, forming the second, largely flat applanation area until the cornea regains its original shape. The second applanation area thus represents an easily recognisable geometric reference point in the sectional images, which may be used for defining the material characteristic by comparing with the first applanation area. A material characteristic of the cornea may be defined or determined particularly by any differences in the diameters of the applanation areas.

The material characteristic of the cornea may be determined even more accurately if an amplitude of the corneal deformation is derived from the sectional images of the cornea. In this way, it is easy to track the precise geometrical progression of the deformation. This means that for any point in time of the deformation, the precise geometrical contour of the deformation subsisting at that time may be recorded, so that the geometrical progression of the deformation may be captured in the manner of a film of the deformation. For example, it is thus possible to capture a clear record even of post-oscillation of the cornea after it springs back, that is to say after the second applanation point.

In order to derive the material characteristic more accurately still, a curvature of the cornea with and/or without deformation may be derived from the sectional images of the cornea. Since the sectional images of the cornea also describe a geometry thereof, particularly before the air puff is applied, the geometry of the cornea may be included in the calculation of the objective intraocular pressure in conjunction with the respective material characteristic of the cornea. This means that the radii of curvature or a curvature of the cornea on an outer and/or inner corneal surface may be derived from the sectional images by image processing. In this context, the radii of curvature may be included as a correction factor when measuring the cornea without deformation and, for example, the thickness of the cornea may be used as a correction factor when measuring with cornea with deformation, thus serving as an indicator for the material characteristic.

The material characteristic of the cornea may be differentiated further if the deformation of the cornea is continued by free vibration of the cornea, and if the free vibration of the cornea is then defined as a further material characteristic. The vibration of the cornea after the air puff is applied and its resumption of its original shape is usually different in different eyes. Thus the vibration of the cornea may also be defined as a further material characteristic of the cornea, and may be used for correcting an intraocular pressure. Accordingly, provision may be made to capture sectional images of the cornea with the observation system that extend beyond the actual corneal deformation so that the vibration or free oscillation of the cornea may be determined.

Free oscillation of the cornea may easily be determined by measuring a frequency and/or amplitude of the free oscillation. In this way, it becomes possible to include the frequency and/or a magnitude of the amplitude and attenuation when defining the further material characteristic.

A stiffness of the cornea may also be derived as a further material characteristic. The concept of stiffness is then explicitly not to be understood as a modulus of elasticity or a Young's modulus, but rather as a material characteristic that is characterized by or responds to a pressure load acting on the eye, that is to say the loading condition that actually exists at the time of a tonometer measurement. Stiffness is thus a direction-dependent parameter of the corneal material. Stiffness is also determined by the corneal material itself and not by other, external influences. Intrinsic stresses that affect the stiffness of the cornea also operate within the corneal material.

Thus, according to a conventional tonometric method a first intraocular pressure may be determined during a single measurement by applying a puff of air. At the same time, the stiffness of the cornea may be derived from the deformation of the cornea that is recorded by the observation system during the deformation. Since the stiffness of the cornea significantly influences a deformation behaviour of the cornea and the measurement of the first intraocular pressure of the eye, allowance may be made for the influence of the cornea on the measurement of the first intraocular pressure. Thus, the previously measured first intraocular pressure may be corrected by the influence of the cornea on the measurement so that an objective intraocular pressure is derived as a result of the measurement. In these circumstances, stiffness of the cornea is essentially an approximately a linear function of the first measured, subjective intraocular pressure of the eye and a measured maximum amplitude of the deformation of the cornea. On a graph of the function of the stiffness, for example, the subjective intraocular pressure may be plotted on a vertical axis, and the maximum amplitude of deformation on a horizontal axis, so that stiffness then has the form of an essentially straight line with a negative gradient. The changes in the measurement values essentially cause a parallel shift in the straight line depending on the measurement values for the horizontal and vertical axes, resulting in differing rigidities in each case. The objective intraocular pressure is derived from the measured stiffness or it may be deduced from the linear stiffness plot from an intersection of the value for subjective intraocular pressure and the value for maximum amplitude with the linear plot for stiffness. During measurement, stiffness of the cornea may always be recalculated as a material characteristic for each measurement, that is to say it is not assumed, as is the case in the prior art, that the material characteristic is a constant for any given eye. Alternatively, the diameters of the applanation area and the deformation area may be used in the graph instead of the amplitudes and used in a similar way.

It may also be particularly advantageous if a series or plurality of sectional images of the cornea is captured during the measurement or cornea deformation process. It this way, it becomes possible to monitor a deformation of the cornea in close detail, and to derive the corresponding material characteristic or an objective intraocular pressure from the progress of the deformation by processing the sectional images.

In addition, a corneal stress may be derived as a further material characteristic that is independent of the intraocular pressure, wherein stresses in the corneal material may be represented visually. The further material characteristic may be defined in the present context as a characteristic that is intrinsic to the material and is unaffected by external influences. A structural characteristic is a characteristic that is affected by external influences in the material, or even by the shape of the material. Thus, provision may be made to render corneal stresses visible by capturing sectional images. In this context, a distinction may be made between stresses that are independent of an intraocular pressure and those that do depend on an intraocular pressure and are created in the corneal material due to the deformation of the cornea. This distinction is made possible by the capture of sectional images that render the stresses in the cornea before deformation and the subsequent stresses in the deformed cornea visible. The intraocular pressure may be corrected and derived taking these stresses into account depending on the type, magnitude, direction and distribution of the stresses in the sectional images of the cornea. In particular, the intraocular pressure may also be corrected by comparing a ratio between the stresses in the cornea before and during deformation, at a defined point or position of the deformed cornea. In a further step of the method, it may be provided that the visibly represented stresses may be compared with visibly represented stresses stored in a database for the purpose of correcting the intraocular pressure. In this way, an objective intraocular pressure or also a corresponding correction value may be known for the values stored in the database, so that the objective intraocular pressure of the eye being measured may be derived with consideration for the corneal stresses.

One photoelastic representation of the cornea may be used as a sectional image in each case. A photoelastic representation makes it easy to display the distribution of stresses in translucent bodies, and it is easy to display the respective distribution and magnitude of mechanical stresses in all parts of the cornea, or even in other translucent areas of the eye, and to evaluate them via image processing. In particular, stresses that occur in the plane of the sectional image may be rendered visible. Stresses that extend transversely to the plane of the sectional image are then ignored, and it is not essential to take these into account for the purpose of correcting the intraocular pressure.

The further material characteristic of the cornea may be derived particularly easily from stress lines on the photoelastic imaging. The stress lines are very clearly visible, and this also makes it easy to distinguish between the further material characteristic of the cornea. The stress lines may be characterised as isochromates or isoclines, isochromates being stress lines that have a constant principal stress differential and isoclines representing stress trajectories of the cornea under a given load. In this way, on the basis of a large number of sectional images obtained during a corneal deformation it is possible to distinguish between stress lines that are changed by the load on the cornea caused by the air puff and stress lines that are present in the cornea due to the shape of the cornea itself and which do not change significantly relative to the cornea.

The analysis system may then be configured in the manner of a polariscope, and the observation system may then comprise an illumination device and a camera device, each of which is equipped with a polariser. For example, it may then be sufficient to provide an appropriate polarisation filter on the illumination device and a polarisation filter on the camera device in order to render stresses in the corneal material visible.

The measurement may be further improved by assigning material characteristics that differ from each other to different areas of the cornea. Thus, assuming that the cornea is of uniform thickness the material characteristics may vary or differ from each other in different regions of a cross-section of the cornea or with reference to a surface area of the cornea.

In an advantageous embodiment of the analysis method, the observation system may comprise a camera and an illumination device in a Scheimpflug arrangement, wherein the sectional images may then be taken with the camera. This means that the camera may be positioned relatively close to an optical axis of a slit lighting device for illuminating the eye in a Scheimpflug arrangement, so that an illuminated sectional image of the eye may be taken with the camera. A camera may also be used as a high-speed camera, for example, capable of capturing at least 4000 images per second. The optical axis of the slit lighting device may also coincide or be congruent with a visual axis of the eye. An effective direction of the air puff may then preferably be coaxial with the optical axis of the slit lighting device.

The opthalmological analysis system according to the invention for measuring an intraocular pressure in an eye, generally, comprises an actuating device with which a cornea of an eye may be deformed in contactless manner, wherein a puff of air may be applied to the eye via the actuating device to cause deformation of the cornea, an observation system with which the deformation of the cornea may be observed and recorded, wherein sectional images are created of the cornea when it is deformed and/or not deformed, and an analysis device with which the intraocular pressure may be derived from the sectional images of the cornea, wherein a material characteristic of the cornea is derived from the sectional images of the cornea in the analysis device, wherein a diameter $d_1$ of a first applanation area of the cornea and a diameter $d_n$ of a deformation area of the cornea that differs from the first applanation area is derived as a material characteristic, wherein the intraocular pressure is derived taking into account the material characteristics of the cornea. With regard to the advantageous effects afforded by the analysis system according to the invention, reference is herewith made to the description of the opthalmological analysis method of the invention.

BRIEF DESCRIPTION OF THE INVENTION

In the following, a preferred embodiment of the invention will be explained in greater detail with reference to the accompanying drawing.

Figure 2:
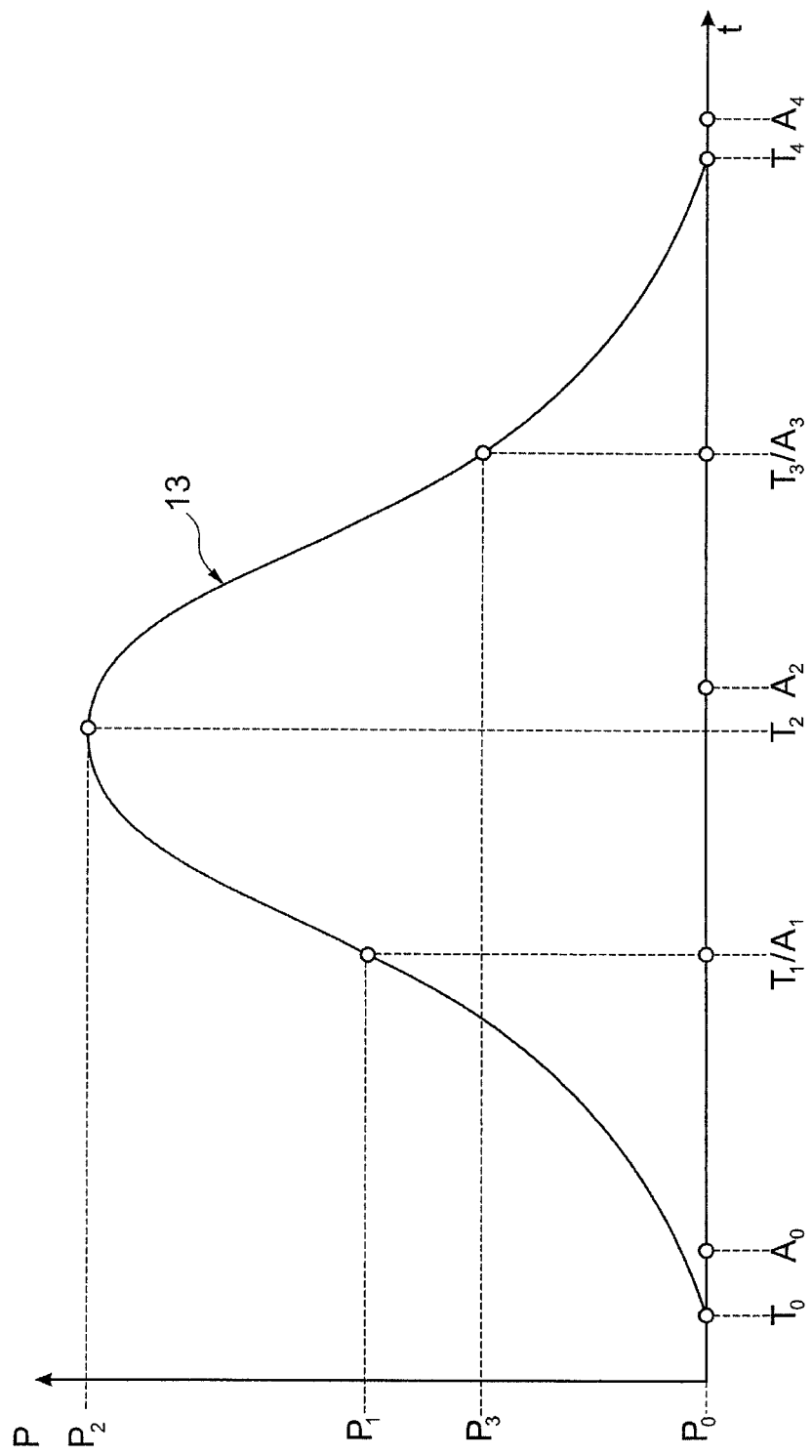
Figure 3:
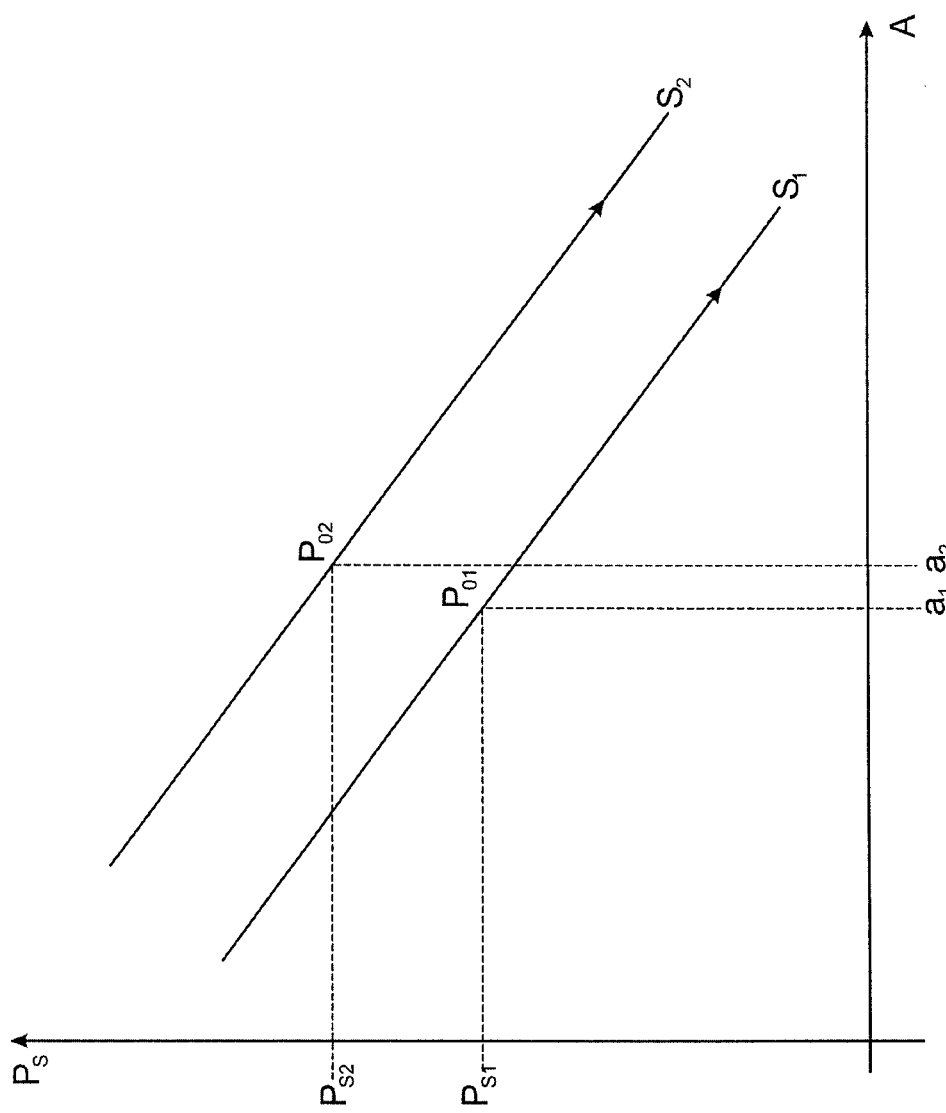
Figure 4A:
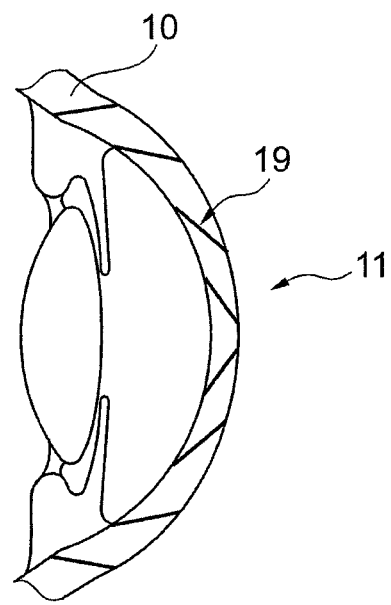
Figure 4B:
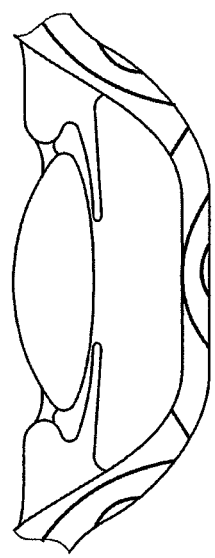

In the drawing:

FIGS. 1a to 1e: show a longitudinal cross-section of a deformation of a cornea of an eye during a measurement;

FIG. 2: is a graph representation of the pump pressure and time during a measurement;

FIG. 3: is a graph representation of the measured intraocular pressure and deformation of a cornea;

FIGS. 4a to 4b: are a visible representation of stresses in the corneal material of the eye.

DETAILED DESCRIPTION OF THE INVENTION

FIGS. 1a to 1e show selected deformation states of a cornea 10 of an eye 11 during a single measurement of an intraocular pressure via an analysis system, not shown here. Each of the drawings is a longitudinal cross-section along an optical axis 12 of eye 11. FIG. 2 is a graph representation with a time t plotted on the horizontal axis and a pump pressure p on the vertical axis. The plot of the pump pressure has the form of a symmetrical bell curve 13, beginning with pump pressure $P_0$ at a start point $T_0$ of the pump, rising to a maximum pump pressure $P_2$ at time $T_2$, and then falling to pump pressure $P_0$ again at an end time $T_4$, which curve is unaffected by the use of an observation system, not shown here, and a Scheimpflug camera with a slit lighting device. The air puff directed at cornea 10 when the pump starts at $T_0$ causes a first deformation of cornea 10 immediately after time $A_0$, which deformation is recordable with the observation system. FIG. 1a represents the shape of cornea 10 at time $A_0$, before it is deformed. As the pump pressure increases, at time $A_1$ cornea is fully applanated as shown in FIG. 1b, wherein an applanation area 14 having diameter $d_1$ is formed, this area being essentially flat and lying in an applanation plane 15. At this point the cornea is offset or indented with respect to apex 16 of cornea 10 by a dimension X. Optionally, but not necessarily, a pump pressure $P_1$ for corresponding time $T_1$ may be calculated for this first applanation point at time $A_1$. After pump pressure $P_2$ is reached, cornea 10 is in the condition of maximum deformation at time $A_2$, as represented in FIG. 1c. In this condition, a point 17 defining a maximum deformation is offset from apex 16 of cornea 10 by a dimension $X_2$. In this case, this therefore represents a maximum deflection of a deformation amplitude. At this maximum deformation amplitude, a diameter $d_2$ of a concave deformation area 18 is formed and recorded. Diameter $d_2$ is defined by a distance between two opposite points of a longitudinal sectional plane of cornea 10, wherein each of the points represents the points of cornea 10 closest to the analysis system. This is followed by a return movement or oscillation of cornea 10, wherein the second applanation point is reached at time $A_3$, as shown in FIG. 1d. At this point, a diameter $d_3$. and a distance $X_3$ are also recorded. It is also optionally possible to determine a pump pressure $P_3$. for matching time point $T_3$. After the pump pressure has fallen back to the original value $P_0$ at time $T_4$, cornea 10 also regains its original condition, as shown in FIG. 1e, at time $A_4$. The deformation states of cornea 10, which are characterized respectively by times $A_0$ to $A_4$, are calculated according to the preceding description of a single measurement of an intraocular pressure of an eye as shown in FIGS. 1a to 1e. In this process, in particular time offsets of the associated time points $A_0$ to $A_4$ and dimensions or indentation depths $X_1$, $X_2$ and $X_3$ are recorded without reference to a pump pressure p, and a stiffness of cornea 10 is derived from these parameters. A measured intraocular pressure is than corrected with a value determined by the stiffness of the cornea, such that an objective intraocular pressure is output as the result of the measurement.

FIG. 3 shows a graph representation with a subjective, measured intraocular pressure on the vertical axis plotted against a deflection amplitude of a maximum deformation of cornea 10 on the horizontal axis. For example, a subjective intraocular pressure on $P_{s1}$ and an amplitude $a_1$, which corresponds to a distance $X_2$ yields a stiffness $S_1$ as an essentially linear function with a downward gradient. However, $S_1$ may also deviate from a linear function and have the form of a line with a relatively large radius of curvature. An objective intraocular pressure $P_{o1}$ may be read off as a variable from the straight line defined by stiffness $S_1$. Similarly, a pressure $P_{se}$ and a deflection $a_2$ also yields parallel shift of the straight line with a stiffness $S_2$ and a further objective intraocular pressure $P_{o2}$ may also be derived from this. Alternatively, diameters $d_1$ and $d_2$ may also be used in the graph instead of amplitudes $a_1$ and $a_2$ and used similarly.

FIGS. 4a to 4b show the deformation states of cornea 10 of eye 11 in similar manner to FIGS. 1a to 1b. Unlike these, however, FIGS. 4a to 4b show the stresses in the corneal material. For example stress lines 19 in the material of cornea 10 are displayed particularly clearly, representing the principal stresses along and transversely to optical axis 12. FIG. 4a thus shows stresses in eye 11 with cornea 10 in a resting position, and FIG. 4b shows stresses in eye 11 with a deformed cornea 10, wherein these stresses differ from the stresses in the resting condition. A comparison of stress based on stress lines 19 thus enables a structural and/or material characteristic of the cornea to be defined, which may be used to correct a measured intraocular pressure and thus also to derive an objective intraocular pressure.

The invention claimed is:

1. An opthalmological analysis method for measuring an intraocular pressure in an eye with an analysis system including an actuating device that deforms a cornea of the eye in contactless manner, the method comprising the following steps:
   (a) applying a puff of air to an eye with an actuating device in such manner that a cornea of the eye is deformed;
   (b) observing and recording a deformation of the cornea with an observation system;
   (c) creating sectional images of the cornea when the cornea is deformed or not deformed according to step (a) with the observation system; and
   (d) deriving an intraocular pressure from the sectional images of the cornea with an analysis device,
   wherein a material characteristic of the cornea is derived from the sectional images of the cornea in the analysis device, wherein a diameter $d_1$ of a first applanation area of the cornea and a diameter $d_n$ of a deformation area of the cornea differing from the first applanation area are derived as the material characteristic, and wherein the intraocular pressure is derived taking into account the material characteristic of the cornea.

2. The analysis method as recited in claim 1, wherein the material characteristic of the cornea is independent of the intraocular pressure.

3. The analysis method as recited in claim 1, wherein a pump pressure for producing the puff of air progresses in the form of a bell curve relative to a duration thereof.

4. The analysis method as recited in claim 1, wherein a maximum pump pressure for creating the puff of air is the same in preceding and following measurements.

5. The analysis method as recited in claim 1, wherein a pump pressure for creating the puff of air is measured when an applanation point of the cornea is reached.

6. The analysis method as recited in claim 1, wherein a speed of movement of the cornea is measured, and wherein the material characteristic is derived from the speed of movement of the cornea.

7. The analysis method as recited in claim 1, wherein a maximum deformation of the cornea is derived from the sectional images, and wherein the material characteristic is derived from the maximum deformation of the cornea.

8. The analysis method as recited in claim 7, wherein a diameter $d_2$ of the deformation area of the cornea is determined for the maximum deformation of the cornea in the direction of an optical axis, and wherein the material characteristic is derived from the diameter $d_2$ of the deformation area of the cornea.

9. The analysis method as recited in claim 1, wherein a parameter of a flat applanation area is measured when an applanation point of the cornea is reached, and wherein the material characteristic is derived from the parameter of the flat applanation area.

10. The analysis method as recited in claim 1, wherein a ratio between the diameter $d_1$ of the first applanation area of the cornea and a diameter $d_3$ of a second applanation area of the cornea is determined, and wherein the material characteristic is derived from the ratio $d_1/d_3$.

11. The analysis method as recited in claim 1, wherein an amplitude of the deformation of the cornea is derived from the sectional images of the cornea, and wherein the material characteristic is derived from the amplitude of the deformation of the cornea.

12. The analysis method as recited in claim 1, wherein a curvature of the cornea with deformation or a curvature of the cornea without deformation or a curvature of the cornea with deformation and a curvature of the cornea without deformation is derived from the sectional images of the cornea, and wherein the material characteristic is derived from the deformation of the curvature of the cornea.

13. The analysis method as recited in claim 1, wherein the deformation of the cornea is continued by a free oscillation of the cornea, and that the free oscillation of the cornea is further determined as the material characteristic.

14. The analysis method as recited in claim 13, wherein a frequency of the free oscillation or an amplitude of the free oscillation or the frequency of the free oscillation and the amplitude of the free oscillation are measured.

15. The analysis method as recited in claim 1, wherein a stiffness of the cornea is derived as the material characteristic.

16. The analysis method as recited in claim 1, wherein a stress in the material of the cornea is derived as the material characteristic.

17. The analysis method as recited in claim 1, wherein material characteristics that differ from each other are each assigned to different regions of the cornea.

18. The analysis method as recited in claim 1, wherein the observation system comprises a camera and an illumination device in a Scheimpflug arrangement, and wherein the sectional images are taken with the camera.

19. An opthalmological analysis system that measures an intraocular pressure in an eye, the opthalmological analysis system comprising:
   (i) an actuating device that can deform a cornea of the eye in contactless manner, wherein the actuating device applies a puff of air to the eye in such manner that the cornea is deformed;
   (ii) an observation system disposed to observe and record the deformation of the cornea, wherein sectional images of the cornea when it is deformed or not deformed are created with the observation system; and
   (iii) an analysis device that derives the intraocular pressure from the sectional images of the cornea,
   wherein a material characteristic of the cornea is derived from the sectional images of the cornea in the analysis device, wherein a diameter $d_1$ of a first applanation area of the cornea and a diameter $d_n$ of a deformation area of the cornea differing from the first applanation area are derived as the material characteristic, and wherein the intraocular pressure is derived taking into account the material characteristic of the cornea.

20. An opthalmological analysis method for measuring an intraocular pressure in an eye with an analysis system including an actuating device that deforms a cornea of the eye in contactless manner, the method comprising the following steps:
   (a) applying a puff of air to an eye with an actuating device in such manner that a cornea of the eye is deformed, wherein the actuating device includes a pump;
   (b) observing and recording a deformation of the cornea with an observation system, wherein the observation system comprises a camera and an illumination device in a Scheimpflug arrangement;
   (c) creating sectional images of the cornea when the cornea is deformed or not deformed according to step (a) with the camera of the observation system; and
   (d) deriving an intraocular pressure from the sectional images of the cornea with an analysis device,
   wherein a material characteristic of the cornea is derived from the sectional images of the cornea in the analysis device, wherein a diameter $d_1$ of a first applanation area of the cornea and a diameter $d_n$ of a deformation area of the cornea differing from the first applanation area are derived as the material characteristic, and wherein the intraocular pressure is derived taking into account the material characteristic of the cornea.

\* \* \* \* \*